US009730707B2

(12) United States Patent
Sasaki

(10) Patent No.: US 9,730,707 B2
(45) Date of Patent: Aug. 15, 2017

(54) SURGICAL INSTRUMENT WITH GRADUATED MARKINGS CORRELATING TO ANGULATION

(71) Applicant: KYPHON SARL, Neuchatel (CH)

(72) Inventor: Neil S. Sasaki, San Jose, CA (US)

(73) Assignee: Kyphon SÀRL, Neuchâtel (CH)

( * ) Notice: Subject to any disclaimer, the term of this patent is extended or adjusted under 35 U.S.C. 154(b) by 403 days.

(21) Appl. No.: 14/464,347

(22) Filed: Aug. 20, 2014

(65) Prior Publication Data

US 2016/0051306 A1 Feb. 25, 2016

(51) Int. Cl.
| A61B 17/16 | (2006.01) |
| A61B 17/88 | (2006.01) |
| A61B 17/34 | (2006.01) |
| A61B 90/00 | (2016.01) |

(52) U.S. Cl.
CPC .......... *A61B 17/1671* (2013.01); *A61B 17/16* (2013.01); *A61B 17/1604* (2013.01); *A61B 17/1631* (2013.01); *A61B 17/1637* (2013.01); *A61B 17/1659* (2013.01); *A61B 17/34* (2013.01); *A61B 17/3472* (2013.01); *A61B 17/88* (2013.01); *A61B 17/8802* (2013.01); *A61B 17/8805* (2013.01); *A61B 17/885* (2013.01); *A61B 17/8811* (2013.01); *A61B 17/8819* (2013.01); *A61B 17/8852* (2013.01); *A61B 2090/062* (2016.02); *A61B 2090/067* (2016.02); *A61B 2090/0811* (2016.02)

(58) Field of Classification Search
CPC . A61B 17/16; A61B 17/1604; A61B 17/1631; A61B 17/1637; A61B 17/1659; A61B 17/1671; A61B 17/34; A61B 17/3472; A61B 17/88; A61B 17/8802; A61B 17/8805; A61B 17/8811; A61B 17/8819; A61B 17/885; A61B 17/8852; A61B 2090/062; A61B 2090/067; A61B 2090/0811

See application file for complete search history.

(56) References Cited

U.S. PATENT DOCUMENTS

| 6,048,346 | A | 4/2000 | Reiley et al. |
| 6,231,615 | B1 | 5/2001 | Preissman |
| 6,241,734 | B1 * | 6/2001 | Scribner ............ A61B 17/8816 606/93 |
| 6,558,390 | B2 | 5/2003 | Cragg |
| 6,592,559 | B1 * | 7/2003 | Pakter ................ A61B 17/3417 604/272 |
| 6,613,054 | B2 | 9/2003 | Scribner et al. |
| 6,719,761 | B1 | 4/2004 | Reiley et al. |
| 6,875,219 | B2 | 4/2005 | Arramon et al. |

(Continued)

*Primary Examiner* — Larry E Waggle, Jr.

(57) ABSTRACT

A surgical instrument includes a first member defining an axis and including an end surface and a passageway. A second member is movably disposed within the passageway and includes a tip and a plurality of spaced apart markings. The second member is movable between a first configuration in which the tip extends parallel to the axis and a second configuration in which the tip extends transverse to the axis. The end surface is aligned with a first one of the markings when the second member is in the first configuration and the end surface is aligned with a second one of the markings when the second member is in the second configuration. Methods are disclosed.

20 Claims, 6 Drawing Sheets

(56) References Cited

U.S. PATENT DOCUMENTS

| | | |
|---|---|---|
| 6,887,246 B2 | 5/2005 | Bhatnagar et al. |
| 7,014,633 B2 | 3/2006 | Cragg |
| 7,066,942 B2 | 6/2006 | Treace |
| 7,141,054 B2 | 11/2006 | Vandewalle |
| 7,704,256 B2 | 4/2010 | Sand et al. |
| 7,713,273 B2 * | 5/2010 | Krueger ............. A61B 17/8811 606/92 |
| 7,744,599 B2 | 6/2010 | Cragg |
| 7,771,431 B2 | 8/2010 | Scribner et al. |
| 7,789,912 B2 | 9/2010 | Manzi et al. |
| 7,799,035 B2 | 9/2010 | Krueger et al. |
| 7,811,291 B2 | 10/2010 | Liu et al. |
| 7,842,041 B2 | 11/2010 | Liu et al. |
| 7,887,543 B2 | 2/2011 | Sand et al. |
| 7,909,833 B2 | 3/2011 | Voellmicke |
| 7,922,690 B2 | 4/2011 | Plishka et al. |
| 7,972,340 B2 | 7/2011 | Sand et al. |
| 8,048,030 B2 | 11/2011 | McGuckin, Jr. et al. |
| 8,052,661 B2 | 11/2011 | McGuckin, Jr. et al. |
| 8,070,728 B2 | 12/2011 | Baroud |
| 8,092,464 B2 | 1/2012 | McKay |
| 8,123,752 B2 | 2/2012 | Zucherman et al. |
| 8,123,756 B2 | 2/2012 | Miller et al. |
| 8,128,633 B2 | 3/2012 | Linderman et al. |
| 8,167,899 B2 | 5/2012 | Justis et al. |
| 8,172,852 B2 | 5/2012 | Zucherman et al. |
| 8,246,627 B2 | 8/2012 | Vanleeuwen et al. |
| 8,282,648 B2 | 10/2012 | Tekulve |
| 8,361,032 B2 | 1/2013 | Krueger et al. |
| 8,366,773 B2 | 2/2013 | Schaller et al. |
| 8,414,571 B2 | 4/2013 | Pellegrino et al. |
| 8,419,730 B2 * | 4/2013 | Pellegrino .......... A61B 17/3472 606/185 |
| 8,500,742 B2 | 8/2013 | Forrest |
| 8,529,576 B2 | 9/2013 | Krueger et al. |
| 8,556,978 B2 | 10/2013 | Schaller |
| 2005/0240171 A1 | 10/2005 | Forrest et al. |
| 2005/0261625 A1 | 11/2005 | Ashman |
| 2006/0293687 A1 | 12/2006 | Bogert |
| 2007/0162042 A1 | 7/2007 | Dunker et al. |
| 2008/0091207 A1 | 4/2008 | Truckai et al. |
| 2009/0105711 A1 | 4/2009 | Mitchell |
| 2009/0149878 A1 | 6/2009 | Truckai et al. |
| 2009/0240293 A1 | 9/2009 | Cragg |
| 2009/0264892 A1 | 10/2009 | Beyar et al. |
| 2010/0094269 A1 | 4/2010 | Pellegrino et al. |
| 2010/0174288 A1 | 7/2010 | Schaller |
| 2010/0298832 A1 * | 11/2010 | Lau .................... A61B 17/1642 606/80 |
| 2011/0004220 A1 | 1/2011 | Krueger et al. |
| 2011/0015574 A1 | 1/2011 | Persat |
| 2011/0196379 A1 | 8/2011 | Blakemore et al. |
| 2012/0046664 A1 | 2/2012 | McGuckin, Jr. et al. |
| 2012/0123427 A1 | 5/2012 | McGuckin, Jr. et al. |
| 2012/0130386 A1 | 5/2012 | McKay |
| 2012/0158004 A1 | 6/2012 | Burger et al. |
| 2012/0179162 A1 | 7/2012 | Tilson et al. |
| 2012/0265210 A1 | 10/2012 | Grinberg et al. |
| 2013/0324997 A1 | 12/2013 | Pellegrino et al. |

* cited by examiner

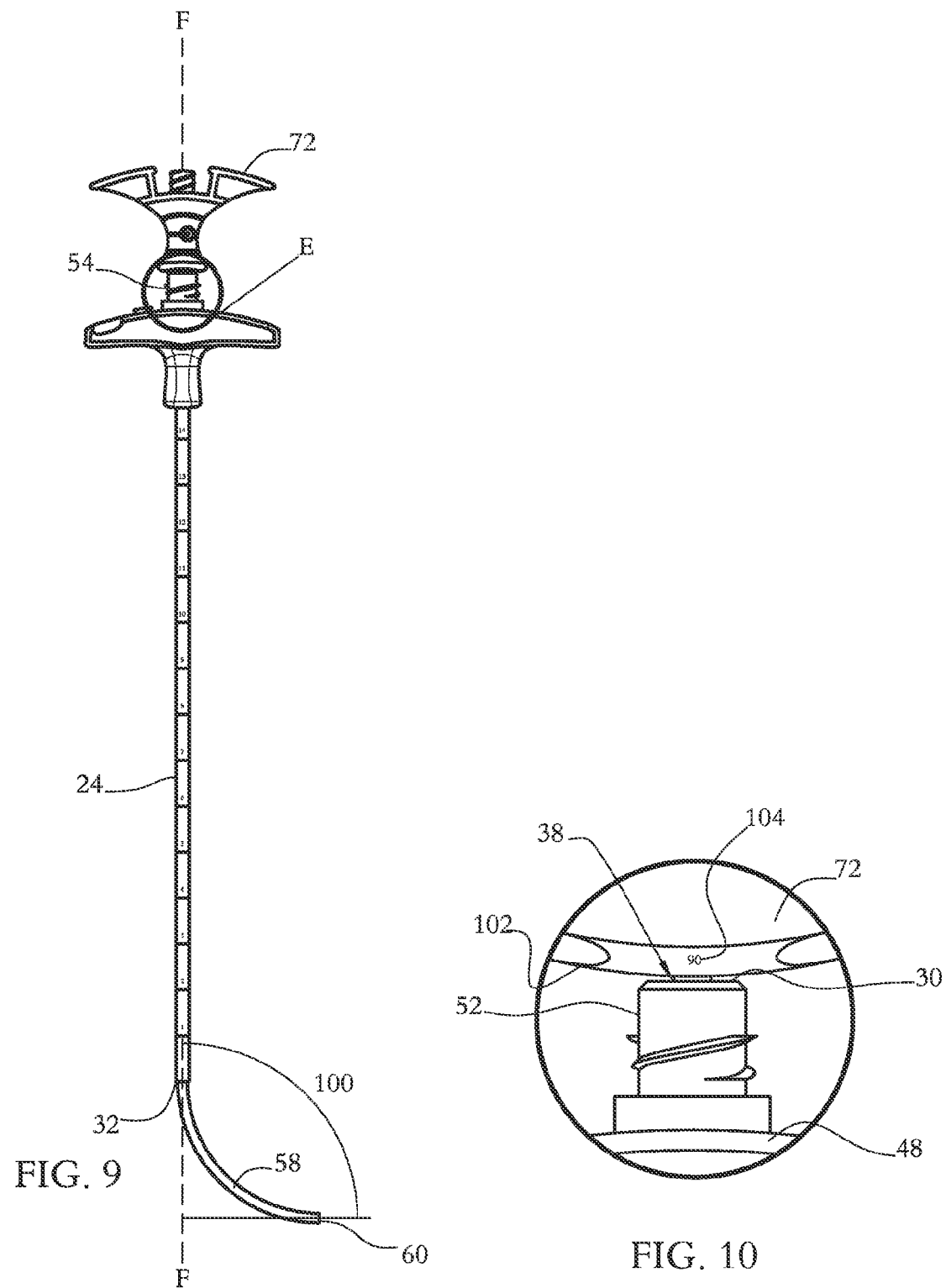

SURGICAL INSTRUMENT WITH GRADUATED MARKINGS CORRELATING TO ANGULATION

TECHNICAL FIELD

The present disclosure generally relates to medical devices for the treatment of musculoskeletal disorders, and more particularly to a surgical system for creating and/or filling bone voids.

BACKGROUND

Height loss is commonly associated with fractures, such as, for example, spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty in which a bone void filler, such as, for example, bone cement is utilized in conjunction with balloon catheter technology. The kyphoplasty procedure restores height of the collapsed spinal bone, which diminishes associated back pain.

Kyphoplasty procedures may also be used to treat fractures in other areas of a patient's body, such as, for example, a distal radius of the patient, such as, for example Colles' fractures. To treat a distal radius fracture using a kyphoplasty procedure, an inflatable bone tamp (IBT) is utilized. The IBT is used to percutaneously reduce comminuted, articular depressions in a controlled manner. Fracture morphologies, such as, for example, "die-punch" fractures are especially suited for correction by an IBT. An IBT is deployed to a surgical site, such as, for example, a bone defect through a working cannula. The IBT creates at least one well-defined void. After the void is created by the IBT, the IBT is removed from the cannula and a material, such as, for example a bone void filler is delivered through the cannula and into the void. This disclosure describes an improvement over these prior art technologies.

SUMMARY

In one embodiment, a surgical instrument is provided. The surgical instrument comprises a first member extending along a longitudinal axis between a first end comprising an end surface and an opposite second end. The first member comprises an inner surface defining a passageway extending along the longitudinal axis. The passageway comprises a first opening at the first end and a second opening at the second end. A second member is movably disposed within the passageway and comprises a first end and an opposite second end comprising a tip. The first end of the second member comprises a plurality of spaced apart markings. The second member is movable between a first configuration in which the tip is disposed within the passageway and extends parallel to the longitudinal axis and a second configuration in which the tip extends through the second opening and extends transverse to the longitudinal axis. The end surface is aligned with a first one of the markings when the second member is in the first configuration and the end surface is aligned with a second one of the markings when the second member is in the second configuration. Methods are provided.

BRIEF DESCRIPTION OF THE DRAWINGS

The present disclosure will become more readily apparent from the specific description accompanied by the following drawings, in which:

FIG. 9 is a side view of components of the system shown in FIG. 1;

FIG. 10 is an enlarged side, view of components of the system shown in FIG. 1 at Detail E in FIG. 9;

DETAILED DESCRIPTION

Figure 1:
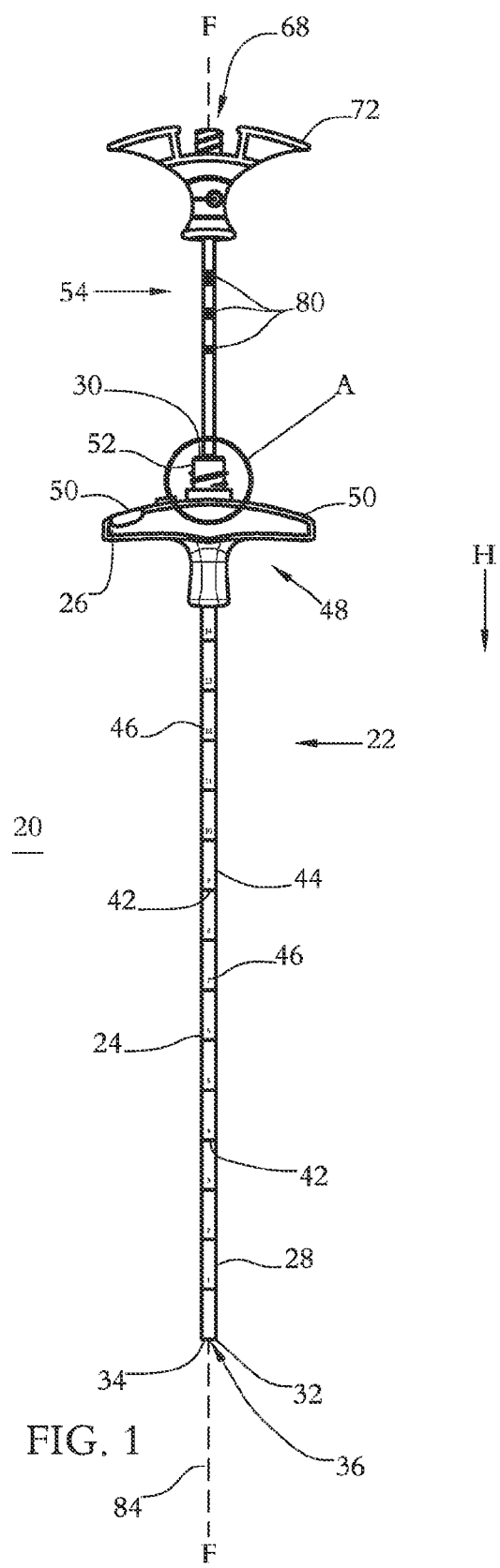
FIG. 1 is a side view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system surgical system for creating and/or filling bone voids.

In one embodiment, the surgical system of the present disclosure is utilized in connection with kyphoplasty or vertebroplasty. The surgical system includes a curved, preformed needle. In some embodiments, the needle comprises nitinol (NiTi). In some embodiments, the needle is cannulated and/or is used to tamp bone and/or deliver cement, such as, for example, bone cement to specific sites in bone. In some embodiments, various amounts of angulation can be created using the needle through a cannula, such as, for example, an introducer cannula to limit the amount of the needle that is exposed (the amount of the needle that is not disposed within the introducer cannula). In some embodiments, limiting the amount of the needle that is exposed allows pre-determined angles to be formed based on the curvature of the needle and exposure distance (the distance the needle extends from the introducer cannula).

In some embodiments, the needle is a pre-set, curved needle that always takes a pre-determined curvature and can be controlled by manipulating the exposed length of the tip of the needle outside the introducer cannula. Because the needles are consistent, markings can be added to the needle to indicate to a user the approximate angle at which the needle extends from the introducer cannula. As such, in some embodiments, the needle includes markings on a shaft of the needle so angulation and exposure distance of the needle can be determined. That is, the markings communicate to a user, such as, for example, a medical practitioner the needle exposure distance and angle. In some embodiments, the markings correlate to pre-determined angles of the needle. In some embodiments, the pre-determined angles are, for example, 15 degrees, 30 degrees, 45 degrees, 60 degrees and 90 degrees. In some embodiments, providing markings on the needle as described herein provides a control feature that makes the disclosed surgical system safer and more effective/controllable.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification, including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-12, there are illustrated components of a surgical system 20 including a surgical instrument 22.

The components of system 20 can be fabricated from biologically acceptable materials suitable for medical applications, including metals, synthetic polymers, ceramics and bone material and/or their composites, depending on the particular application and/or preference of a medical practitioner. For example, the components of system 20, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, lastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polypeptide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

System 20 is employed, for example, with an open or mini-open, minimal access and/or minimally invasive including percutaneous surgical technique to remove tissue, such as, for example, nucleus pulposus tissue from a vertebral body of a patient in connection with a discectomy procedure.

Figure 11:
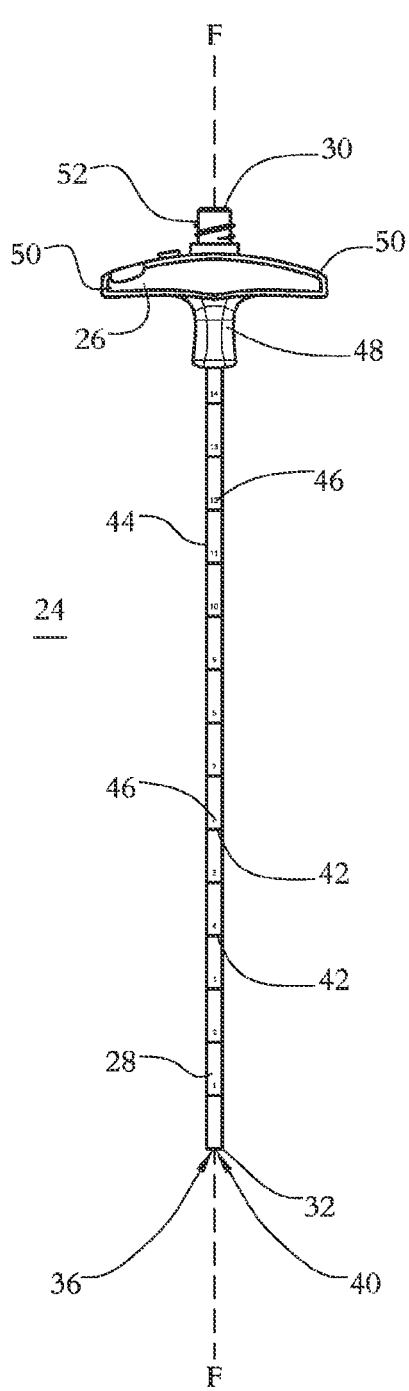
FIG. 11 is a side view of a component of the system shown in FIG. 1.

Instrument 22 includes a first member, such as, for example, a cannula 24 extending along a longitudinal axis F between an end 26 and an opposite end 28, as shown in FIGS. 1 and 11, for example. End 26 comprises an end surface 30 and end 28 comprises an end surface 32 opposite surface 30. Surfaces 30, 32 extend perpendicular to axis F. Cannula 24 comprises an inner surface 34 defining a passageway 36 extending along axis F having a cylindrical cross sectional configuration, as shown in FIG. 1, for example. In some embodiments, at least a portion of cannula 24 is transparent to facilitate visualization of items within passageway 36. Cannula 24 comprises a circular opening 38 at end 26 that extends through surface 30 and a circular opening 40 at end 28 that extends through surface 32. Openings 38, 40 are each coaxial with axis F and are in communication with passageway 36. In some embodiments, passageway 36, opening 38 and/or opening 40 may have various cross section configurations, such as, for example, oval, oblong, triangular, rectangular, square, polygonal, irregular, uniform, non-uniform, variable, tubular and/or tapered. In some embodiments, surface 30 and/or surface 32 may be disposed at alternate orientations, relative to axis F, such as, for example, transverse, perpendicular and/or other angular orientations such as acute or obtuse, co-axial and/or may be offset or staggered. In some embodiments, cannula 24 comprises a rigid material that is resistant to bending (e.g. would break if bent). In some embodiments, cannula 24 comprises a flexible material. In some embodiments, surface 32 is blunt and/or rounded to prevent injury to tissue, such as, for example, soft tissue or bone. In some embodiments, surface 32 defines a sharp edge configured to penetrate tissue in response to pushing or twisting forces applied at end 26.

In some embodiments, cannula 24 comprises a plurality of spaced apart measured depth indicators 42, as shown in FIG. 1, for example. In some embodiments, indicators 42 correlate to a distance between surface 32 and a respective one of indicators 42. That is, indicators 42 are pre-positioned along the length of cannula 24 at intervals that mark the extent to which cannula 24 has been inserted into a cavity. For example, indicators 42 permit a medical practitioner to visually determine the depth of cannula 24 within, for example, an incision in a patient and/or a bone or other anatomical structure, without measuring cannula 24. In some embodiments, indicators 42 comprise annular bands that extend circumferentially about an outer surface 44 of cannula 24. In some embodiments, indicators 42 extend perpendicular to axis F. In some embodiments, at least one of indicators 42 include indicia 46 correlating to a distance between surface 32 and a respective one of indicators 42. In some embodiments, indicia 46 is one or more letters, words or numbers correlating to the distance between surface 32 and a respective one indicators 42. In some embodiments, indicia 46 correlate to units of measurement, such as, for example, millimeters, centimeters, inches, etc. In some embodiments, indicia 46 are consecutively numbered, beginning at end 28.

In some embodiments, end 26 includes a handle 48 comprising a top end that defines surface 30, as shown in FIGS. 1 and 11, for example. Handle 48 is fixed relative to surface 44. Passageway 36 extends through handle 48. Handle 48 comprises arms 50 that extend transverse to axis F configured for gripping by a medical practitioner to move cannula 24 along axis F and/or rotate cannula 24 about axis F. In some embodiments, handle 48 is made from a molded or cast rigid plastic or metal material. In some embodiments, handle 48 is shaped to be comfortably and securely grasped by a normal human hand. In some embodiments, handle 48 is configured to fit comfortably across the palm of the normal human hand. In some embodiments, handle 48 includes a threaded post 52, shown in FIGS. 1 and 2, for example, configured to engage another component of system 20, such as, for example, a stylet, cannula, bone tamp, etc. to couple such components to cannula 24. In some embodiments, the component can be variously connected with cannula 24, such as, for example, monolithic, integral connection, frictional engagement, threaded engagement, mutual grooves, screws, adhesive, nails, barbs and/or raised element.

Figure 12:
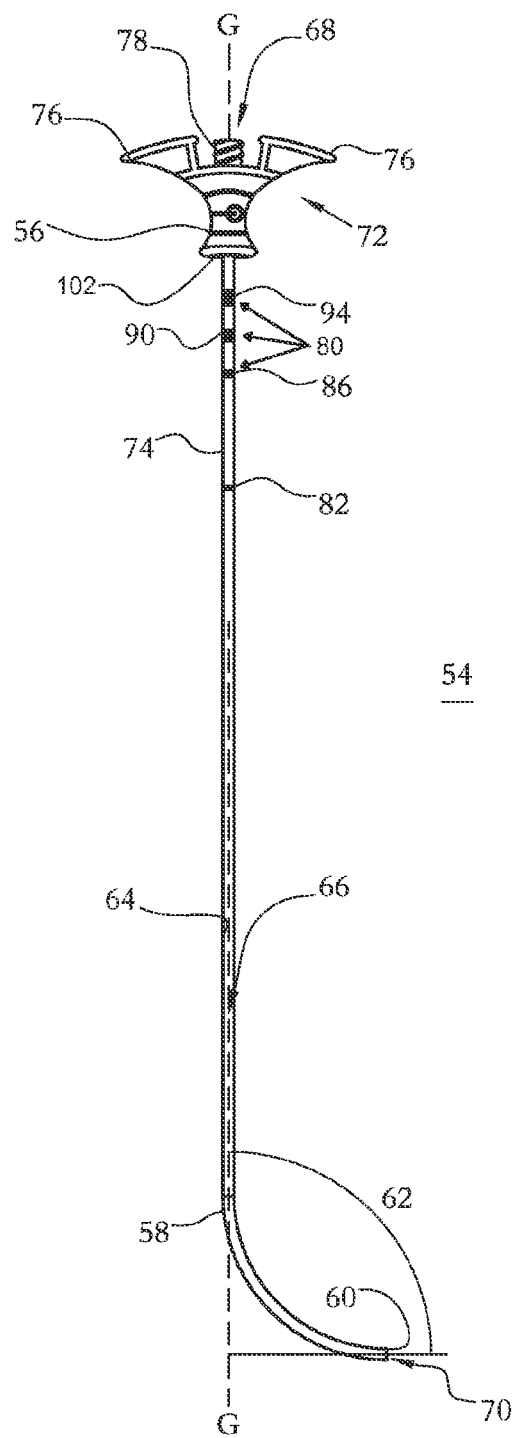
FIG. 12 is a side view of a component of the system shown in FIG. 1, in part phantom.

A second member, such as, for example, a needle 54 is slidably disposed within passageway 36, as shown in FIG. 1, for example. Needle 54 extends between an end 56 and an opposite end 58 along a longitudinal axis G, as shown in FIG. 12. End 58 includes an end-most tip 60. Needle 54 is pre-bent or pre-formed to have a pre-determined curvature. In some embodiments, needle 54 comprises a shape memory material, such as, for example, nitinol or perforated spring steel to allow needle 54 to return to the pre-determined curvature after being temporarily straightened. In some embodiments, the shape memory material has a one-way memory effect. In some embodiments, the shape memory material has a two-way memory effect. In some embodiments, the shape memory material is a polymer or an alloy. In some embodiments, the shape memory material is copper-based or iron-based. In some embodiments, needle 54 is pre-bent such that tip 60 extends at an angle 62 relative to axis G, as shown in FIG. 12. In some embodiments, angle 62 is an angle in a range between about 45 degrees and 90 degrees. In some embodiments, angle 62 is a 90 degree angle. In some embodiments, needle 54 is pre-bent such that tip 60 may be disposed at alternate orientations, relative to axis G, such as, for example, transverse, perpendicular and/or other angular orientations such as acute or obtuse, co-axial and/or may be offset or staggered.

In some embodiments, needle 54 comprises an inner surface 64 defining a channel, such as, for example, a lumen 66 extending between and through ends 56, 58, as shown in FIG. 12. End 56 includes a circular opening 68 extending through end 56 and end 58 includes a circular opening 70 extending through tip 60, as also shown in FIG. 12. Openings 68, 70 are in communication with lumen 66. In some embodiments, lumen 66 has a cylindrical cross sectional configuration that is uniform along the length of needle 54. In some embodiments, lumen 66, opening 68 and/or opening 70 variously shaped, such as, for example, oval, oblong, triangular, square, polygonal, irregular, uniform, non-uniform, offset, staggered, undulating, arcuate, variable and/or tapered. In some embodiments, needle 54 is configured to deliver a material, such as, for example, a bone cement to a surgical site such that the material can be inserted into opening 68, move through lumen 66 and exit lumen 66 through opening 70.

In some embodiments, end 56 comprises a handle 72, as shown in FIG. 12, for example. Handle 72 is fixed relative to an outer surface 74 of needle 54. Lumen 66 extends through handle 72. Handle 72 comprises arms 76 that extend transverse to axis G configured for gripping by a medical practitioner to move needle 54 relative to cannula 24 along axis G and/or rotate needle 54 about axis G. In some embodiments, handle 72 is made from a molded or cast rigid plastic or metal material. In some embodiments, handle 72 is shaped to be comfortably and securely grasped by a normal human hand. In some embodiments, handle 72 is configured to fit comfortably across the palm of the normal human hand. In some embodiments, handle 72 includes a threaded post 78 configured to engage another component of system 20, such as, for example, an end of a material source, such as, for example, a syringe, to couple such the material source to needle 54. In some embodiments, the material source can be variously connected with needle 54, such as, for example, monolithic, integral connection, frictional engagement, threaded engagement, mutual grooves, screws, adhesive, nails, barbs and/or raised element.

In some embodiments, rather than include lumen 66, needle 54 is solid. That is, needle 54 has a solid configuration does not include any passageways, lumens or openings extending therethrough. This allows needle 54 to be used as a bone tamp, for example. In such embodiments, tip may blunt or rounded to selectively move bone. In some embodiments, tip 60 includes a sharp edge configured to remove, cut and/or scrape tissue, such as, for example, cancellous bone or cortical bone. In some embodiments, tip 60 includes a thread form, such as, for example a helical thread form configured to remove, cut and/or scrape tissue, such as, for example, cancellous bone or cortical bone.

Various amounts of angulation can be created by moving needle 54 relative to cannula 24 to control and/or limit the amount of needle 54 that is positioned outside of passageway 36. Controlling/limiting the amount of needle 54 that extends outside of passageway 36 allows predetermined angles to be formed based on the curvature of needle 54 and the distance tip 60 extends from surface 32. Needle 54 therefore includes markings 80 at end 56, shown in FIGS. 1 and 11, for example, to determine angulation and exposure distance of needle 54. That is, markings 80 communicate to a user, such as, for example, a medical practitioner the length of needle 54 that extends from surface 32. Because needle 54 is pre-bent in a known configuration, there is a direct relationship between the distance tip 60 extends from surface 32 and the angle at which tip 60 extends relative to axis F. For example, when the length of needle 54 that extends from surface 32 is length X, tip 60 will always extend at an angle Y relative to axis F. As such, a marking 80 that aligns with surface 30 when tip extends the distance X from surface 32 indicates that tip 60 extends at angle Y relative to axis F. Markings 80 thus correlate to pre-determined angles of tip 60 relative to axis F.

Figure 2:
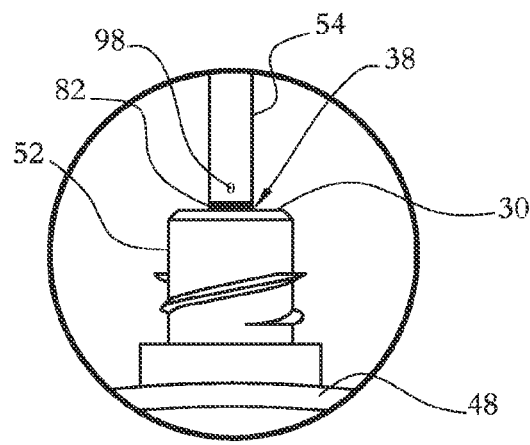
FIG. 2 is an enlarged view of components of the system shown in FIG. 1 at Detail A in FIG. 1.
Figure 3:
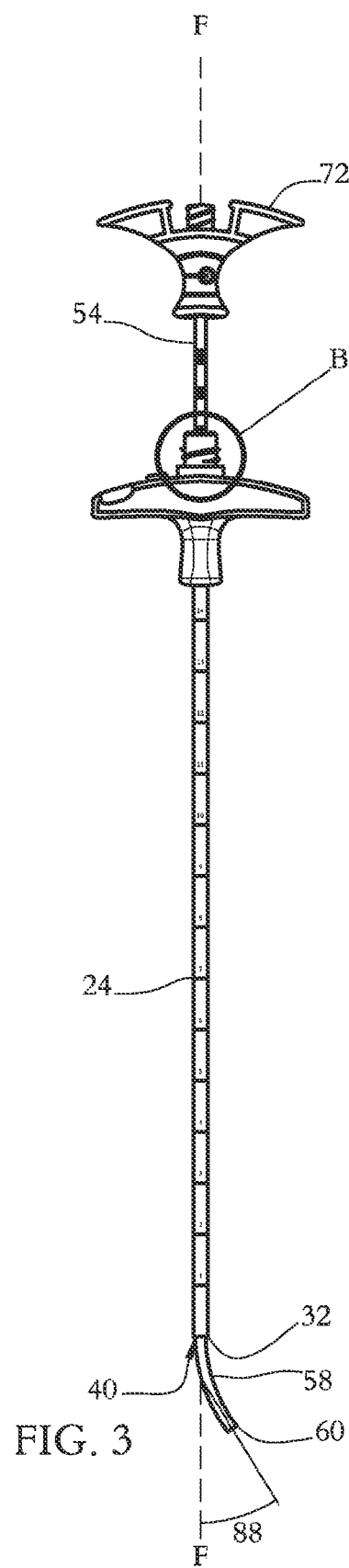
FIG. 3 is a side view of components of the system shown in FIG. 1.
Figure 4:
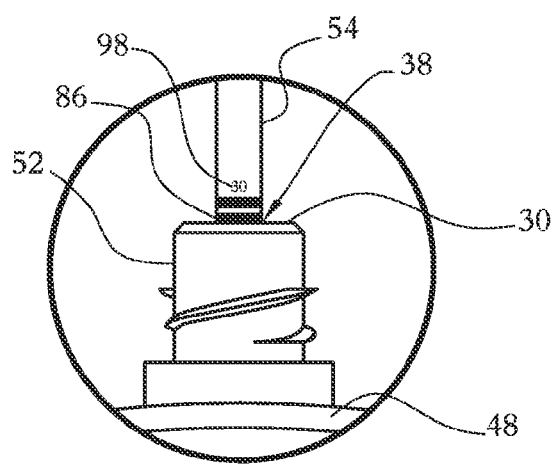
FIG. 4 is an enlarged side, view of components of the system shown in FIG. 1 at Detail B in FIG. 3.
Figure 5:
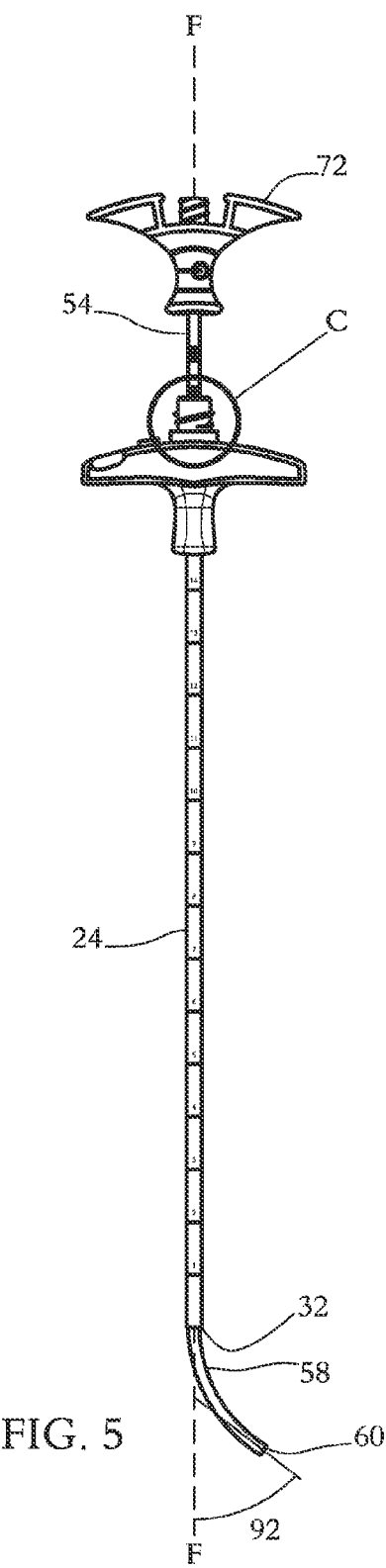
FIG. 5 is a side view of components of the system shown in FIG. 1.
Figure 6:
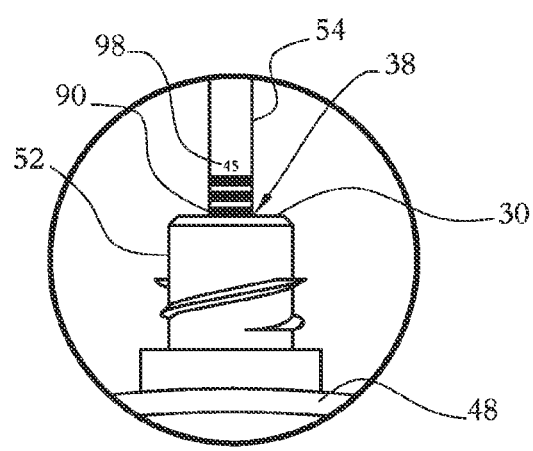
FIG. 6 is an enlarged side, view of components of the system shown in FIG. 1 at Detail C in FIG. 5.
Figure 7:
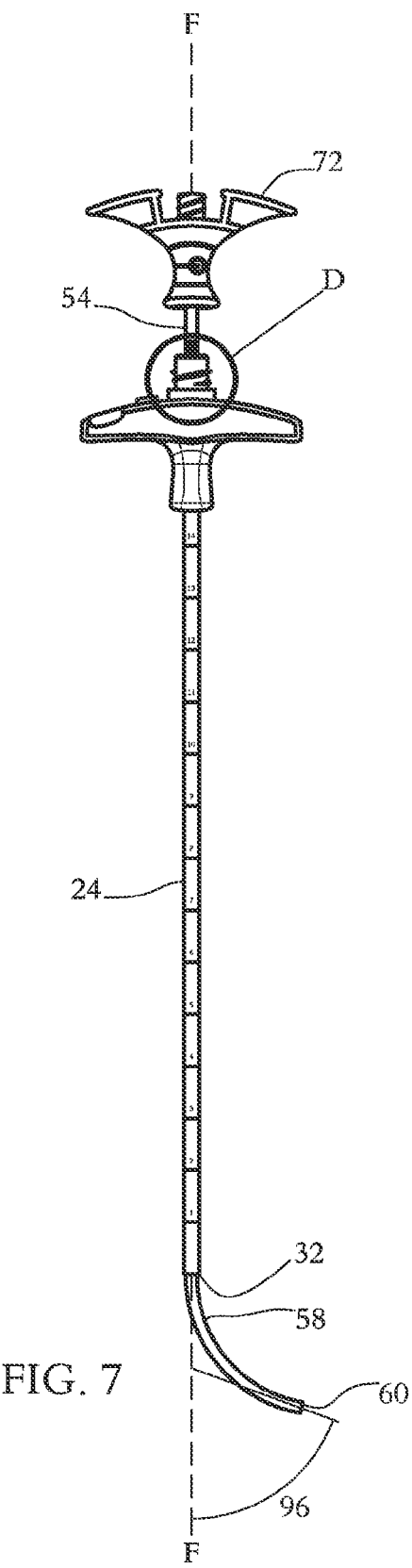
FIG. 7 is a side view of components of the system shown in FIG. 1.
Figure 8:
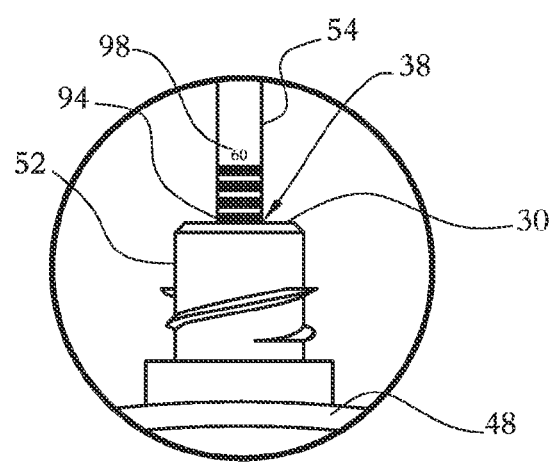
FIG. 8 is an enlarged side, view of components of the system shown in FIG. 1 at Detail D in FIG. 7.

In some embodiments, markings 80 correlate to pre-determined angles of, for example, 0 degrees, 15 degrees, 30 degrees, 45 degrees, 60 degrees and 90 degrees. In some embodiments, the pre-determined angles are any angle between about 0 degrees and about 90 degrees. In some embodiments, markings 80 include a first marking 82 that indicates when tip 60 extends at an angle 84 relative to axis F (as shown in FIGS. 1 and 2), a second marking 86 that indicates when tip 60 extends at an angle 88 relative to axis F (as shown in FIGS. 3 and 4), a third marking 90 that indicates when tip 60 extends at an angle 92 relative to axis F (as shown in FIGS. 5 and 6) and a fourth marking 94 that indicates when tip 60 extends at an angle 96 relative to axis F (as shown in FIGS. 7 and 8).

In some embodiments, angles 84, 88, 92, 96 are each between about 0 degrees and 90 degrees. In some embodiments, angle 84 is about 0 degrees, angle 88 is about 1 to about 30 degrees, angle 92 is about 31 to about 45 degrees and angle 96 is about 46 to about 60 degrees. In some embodiments, angle 84 is about 0 degrees, angle 88 is about 30 degrees, angle 92 is about 45 degrees and angle 96 is about 60 degrees. In some embodiments, marking 82 includes a single band extending circumferentially about surface 74, marking 86 includes two spaced apart bands extending circumferentially about surface 74, marking 90 includes three spaced apart bands extending circumferentially about surface 74 and marking 94 includes four spaced apart bands extending circumferentially about surface 74 to allow a medical practitioner to distinguish between markings 82, 86, 90, 94 visually. In some embodiments, at least one of markings 82, 86, 90, 94 include indicia 98 correlating to the angle of tip 60 relative to axis F when a respective one of markings 82, 86, 90, 94 are aligned with surface 30. In some embodiments, indicia 98 include numbers that indicate the angle of tip 60 relative to axis F when a respective one of markings 82, 86, 90, 94 are aligned with surface 30.

In some embodiments, needle 54 includes one or a plurality of markings 80. In some embodiments, a medical practitioner may add at least one additional marking 80 by measuring the angle tip 60 extends relative to axis F and then adding the additional marking 80 such that the additional marking 80 aligns with surface 30. Indicia 98 may also be added to indicate the angle tip 60 extends relative to axis F when the additional marking is aligned with surface 30. In some embodiments, the additional marking 80 indicates an angle of tip 60 relative to axis F between about 0 degrees and about 90 degrees. This allows a medical practitioner to provide instrument 22 with markings relevant to a particular surgical procedure. For example, if the medical practitioner desires tip 60 to extend relative to axis F at an angle X, the medical practitioner can position tip 60 such that tip extends X degrees relative to axis F and add an additional marking 80 to needle 54 such that the additional marking 80 is aligned with surface 30 when tip 60 extends at angle X relative to axis F.

Due to the direct relationship between the length of needle 54 that extends from surface 32 and the angle at which tip 60 extends relative to axis F, the length of needle 54 that extends from surface 32 when an end surface 102 of handle 72 engages surface 30 can be determined by measuring an angle 100 at which tip 60 extends relative to axis F (see, for example, FIGS. 9 and 10). In some embodiments, angle 100 is between about 61 degree and about 90 degrees. In some embodiments, angle 100 is between about 1 degree and about 90 degrees. In one embodiment, angle 100 is 90 degrees. In some embodiments, handle 72 includes indicia 104 correlating to the angle of tip 60 relative to axis F when surface 102 engages surface 30. In some embodiments, indicia 104 include numbers that indicate the angle of tip 60 relative to axis F when surface 102 engages surface 30.

Needle 54 is movable between a first configuration in which tip 60 is disposed within passageway 36 and tip 60 extends parallel to axis F, as shown in FIG. 1 and a second configuration in which tip 60 extends through opening 40 such that tip 60 is positioned outside of passageway 36 and extends transverse to axis F, as shown in FIGS. 3, 5, 7 and 9. When needle 54 is in the first configuration, marking 82 is aligned with surface 30, as shown in FIG. 2. Needle 54 is moved from the first configuration to the second configuration by translating needle 54 relative to cannula 24 in the direction shown by arrow H in FIG. 1. The amount that needle 54 is translated relative to cannula 24 is dependent upon the angle at which the medical practitioner desires tip 60 to extend relative to axis F. It will be appreciated that needle 54 may move from a configuration in which one of markings 80 is aligned with surface 30 to a configuration in which another one of markings 80 is aligned with surface 30, as desired by a medical practitioner. In some embodiments, moving needle 54 between configurations in which surface 30 is aligned with different markings 80 may be referred to as moving needle 54 from the second configuration to a third configuration to make clear that needle 54 is being moved relative to cannula 24.

In assembly, operation and use, system 20, similar to the systems and methods described herein, includes instrument 22 and is employed with a surgical procedure for treatment of a spinal disorder affecting a section of a spine of a patient, as discussed herein. System 20 is employed with a surgical procedure for treatment of a condition or injury of an affected section of the spine including vertebrae.

In use, to treat the affected section of the spine, a medical practitioner obtains access to a surgical site including the vertebrae in any appropriate manner, such as through incision and retraction of tissues. In some embodiments, the components of system 20 may be used in any existing surgical method or technique including open surgery, mini-open surgery, minimally invasive surgery including percutaneous surgical implantation, whereby the vertebrae are accessed through a micro-incision, or sleeve that provides a protected passageway to the area. Once access to the surgical site(s) is obtained, the particular surgical procedure is performed for treating the spinal disorder. The components of system 20 including instrument 22 are employed to augment the surgical treatment. Instrument 22 can be delivered as a pre-assembled device or can be assembled in situ. System 20 may be may be completely or partially revised, removed or replaced.

In some embodiments, system 20 can include one or more surgical instruments for use with instrument 22, such as, for example, drivers, inserters, extenders, reducers, spreaders, distractors, blades, retractors, clamps, forceps, elevators and drills, which may be alternately sized and dimensioned, and arranged as a kit.

An incision is made into the patient. Instrument 22 is inserted into the incision with needle 54 in the first configuration. Instrument 22 is positioned such that end 28 is adjacent a surgical site. Needle 54 is selectively moved from the first configuration to the second configuration such that one of markings 80 is aligned with surface 30. The marking 80 that aligns with surface 30 is dependent on the angle the medical practitioner wishes tip 60 to extend relative to axis F. For example, if the medical practitioner wishes to have tip 60 extend at angle 88 relative to axis F, the medical practitioner would translate needle 54 relative to cannula 24 until marking 86 is aligned with axis F, as shown in FIG. 4. If the medical practitioner wishes to have tip 60 extend at angle 92 relative to axis F, the medical practitioner would translate needle 54 relative to cannula 24 until marking 90 is aligned with axis F, as shown in FIG. 6. If the medical practitioner wishes to have tip 60 extend at angle 96 relative to axis F, the medical practitioner would translate needle 54 relative to cannula 24 until marking 94 is aligned with axis F, as shown in FIG. 8. If the medical practitioner wishes to have tip 60 extend at angle 100 relative to axis F, the medical practitioner would translate needle 54 relative to cannula 24 until surface 102 engages surface 30, as shown in FIG. 10. Once needle 54 is in the second configuration, the medical practitioner may manipulate cannula 24 and/or needle 54, such as, for example via handles 48, 72, to move tip 60 relative to the surgical site. In some embodiments, where needle 54 is a bone tamp, for example, tip 60 may then be used to selectively position tissue, such as, for example, bone. Upon completion of a procedure, instrument 22 is removed and the incision(s) are closed.

In some embodiments, needle 54 is used to deliver a material, such as, for example, a bone cement. An incision is made into the patient. A cavity forming device, such as, for example, an inflatable bone tamp, is inserted into the incision and positioned adjacent a surgical site, with a balloon of the inflatable bone tamp in an unexpanded or uninflated position. The inflatable bone tamp is moved from the unexpanded or uninflated position to an expanded or inflated position. As the inflatable bone tamp moves from the unexpanded or uninflated position to the expanded or inflated position, the balloon selectively positions tissue, such as, for example, bone, so as to create a cavity. Instrument 22 is inserted into the incision with needle 54 in the first configuration. Instrument 22 is positioned such that end 28 is adjacent the cavity formed by the balloon. Needle 54 is selectively moved from the first configuration to the second configuration such that one of markings 80 is aligned with surface 30, as discussed above. Once needle 54 is in the second configuration, needle 54 engages a material source, such as, for example, a source of bone cement. In some embodiments, the material source is threaded with post 52 to couple the material source to needle 54. The bone cement is delivered from the material source and through opening 68 such that the bone cement moves through lumen 66 and exits needle 54 through opening 70. Enough bone cement is delivered to partially or completely fill the cavity created by the balloon. Upon completion of a procedure, instrument 22 is removed and the incision(s) are closed.

In some embodiments, needle 54 has a solid configuration (is not cannulated) and is configured to form a hole in tissue, such as, for example, bone. In such embodiments, needle 54 is moved from the first configuration to the second configuration. Needle 54 is then rotated about axis F such that cutting features, such as, for example, blades, threads, etc. of needle 54 cut into the tissue to form a recess therein. In some embodiments, a component of system 20, such as, for example, an implant, such as, for example, a bone screw, may be inserted into the recess. In some embodiments, a surgical procedure may be performed in the recess.

One or more of the components of system 20 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 20.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical instrument, comprising:
   a first member extending along a longitudinal axis between a first end having an end surface and an opposite second end, the first member having an inner surface defining a passageway extending along the longitudinal axis and an outer surface, the passageway having a first opening at the first end of the first member and a second opening at the second end of the first member, the first member including a handle at the first end of the first member; and a second member movably disposed within the passageway of the first member and having a first end and an opposite second end with a tip, at least a portion of the second end of the second member being pre-bent, the second member including a handle at the first end, the handle of the first member and the handle of the second member being configured to cooperatively engage each other to limit movement of the second member within the passageway of the first member, the first end of the second member having a plurality of spaced apart markings indicating an exposure distance of the tip and a corresponding plurality of spaced apart indicia indicating an angle of the tip relative to the longitudinal axis of the first member, wherein the second member is movable between a first configuration in which the tip is disposed within the passageway and extends parallel to the longitudinal axis and a second configuration in which the tip extends through the second opening of the passageway and extends transverse to the longitudinal axis, wherein the end surface of the first end of the first member is aligned with a first marking of the plurality of spaced apart markings when the second member is in the first configuration and the end surface of the first end of the first member is aligned with a second marking of the plurality of spaced apart markings when the second member is in the second configuration, and wherein the handle of the first member and the handle of the second member when cooperatively engaged are lockable to maintain a selected exposure distance and angle of the tip.

2. A surgical instrument as recited in claim 1, wherein the handle of the first member includes a post having a threaded exterior surface, the handle of the second member including a post having a threaded interior surface that frictionally engages the threaded exterior surface of the post of the first member.

3. A surgical instrument as recited in claim 1, wherein the second member is formed of a shape memory material.

4. A surgical instrument as recited in claim 3, wherein the shape memory material is nitinol.

5. A surgical instrument as recited in claim 1, wherein the second member is formed of perforated spring steel.

6. A surgical instrument as recited in claim 1, wherein the second member has an inner surface defining a channel, the channel having a first opening at the first end of the second member and a second opening at the second end of the second member.

7. A surgical instrument as recited in claim 1, wherein the second member is a bone tamp.

8. A surgical Instrument as recited in claim 1, wherein:
the tip extends at a first angle relative to the longitudinal axis when the second member Is in the second configuration;
the second member is movable from the second configuration to a third configuration in which the tip extends through the second opening of the passageway and extends at a second angle relative to the longitudinal axis, the second angle being greater than the first angle; and the end surface of the first end of the first member engages an end surface of the handle of the second member when the second member is in the third configuration.

9. A surgical instrument as recited in claim 8, wherein:
the first angle is between 1 and 89 degrees; and
the tip extends at the second angle to the longitudinal axis when the second member is in the third configuration, the second angle being 90 degrees.

10. A surgical instrument as recited in claim 8, wherein:
the second marking of the plurality of spaced apart markings is predetermined to align with the end surface of the first end of the first member when the tip extends at the first angle relative to the longitudinal axis; and
the end surface of the first end of the first member is predetermined to engage the end surface of the handle of the second member when the tip extends at the second angle relative to the longitudinal axis.

11. A surgical instrument as recited in claim 1, wherein the first member has a plurality of spaced apart indicators each correlating to a distance between a second end surface of the first member and a respective indicator of the plurality of spaced apart indicators.

12. A surgical method comprising:
providing a surgical instrument comprising:
a first member extending along a longitudinal axis between a first end having an end surface and an opposite second end, the first member having an inner surface defining a passageway extending along the longitudinal axis and an outer surface, the passageway having a first opening at the first end of the first member and a second opening at the second end of the first member, the first member including a handle at the first end of the first member; and
a second member movably disposed within the passageway of the first member and having a first end and an opposite second end with a tip, at least a portion of the second end of the second member being pre-bent, the second member including a handle at the first end, the handle of the first member and the handle of the second member being configured to cooperatively engage each other to limit movement of the second member within the passageway of the first member, the first end of the second member having a plurality of spaced apart markings indicating an exposure distance of the tip and a corresponding plurality of spaced apart indicia indicating an angle of the tip relative to the longitudinal axis of the first member;
forming an incision defining a pathway to a surgical site;
inserting the second end of the first member into the Incision with the second member in the first configuration such that the second end of the first member is positioned adjacent the surgical site;
moving the second member from a first configuration in which the tip is disposed within the passageway and extends parallel to the longitudinal axis to a second configuration in which the tip extends through the second opening of the passageway and extends transverse to the longitudinal axis;
aligning the end surface of the first member with a first marking of the plurality of spaced apart markings when the second member is in the first configuration and the end surface of the first member with a second marking of the plurality of spaced apart markings when the second member is in the second configuration, and locking the handle of the first member and the handle of the second member when cooperatively engaged to maintain a selected exposure distance and angle of the tip.

13. A method as recited in claim 12, wherein:

the tip extends at a first angle relative to the longitudinal axis when the second member is in the second configuration;

the method further comprises moving the second member from the second configuration to a third configuration in which the tip extends through the second opening of the passageway and extends at a second angle relative to the longitudinal axis, the second angle being greater than the first angle; and wherein the end surface of the first member engages an end surface of the handle of the second member when the second member is in the third configuration.

14. A method as recited in claim 12, wherein:

the second member comprises an inner surface defining a channel, the channel having a first opening at the first end of the second member and a second opening at the second end of the second member; and the method further comprises injecting bone cement through the first opening of the second member into the channel and out of the second opening of the second member to position the bone cement adjacent the surgical site.

15. A method as recited in claim 12, wherein:

the tip extends at a first angle relative to the longitudinal axis when the second member is in the second configuration; and the method further comprises:

moving the second member from the second configuration to a third configuration in which the tip extends through the second opening of the passageway and extends at a second angle relative to the longitudinal axis, the second angle being greater than the first angle; and creating an additional marking on the second member that aligns with the end surface of the first member while the second member is in the third configuration such that the additional marking correlates to the tip extending at the second angle relative to the longitudinal axis.

16. A surgical instrument, comprising:

a first member extending along a longitudinal axis between a first end having an end surface and an opposite second end, the first member having an inner surface defining a passageway extending along the longitudinal axis and an outer surface, the passageway having a first opening at the first end of the first member and a second opening at the second end of the first member, the first member including a handle at the first end of the first member; and a second member movably disposed within the passageway of the first member and having a first end and an opposite second end with a tip extending through the second opening of the passageway, at least a portion of the second end of the second member being pre-bent, the second member including a handle at the first end, the handle of the first member and the handle of the second member being configured to cooperatively engage each other to limit movement of the second member within the passageway of the first member, the first end of the second member having a plurality of spaced apart markings indicating an exposure distance of the tip and a corresponding plurality of spaced apart indicia indicating an angle of the tip relative to the longitudinal axis of the first member, wherein the second member is movable between a first configuration in which the tip extends at a first angle relative to the longitudinal axis and a second configuration in which the tip extends at a second angle relative to the longitudinal axis, wherein the end surface of the first member is aligned with a first marking of the plurality of spaced apart markings when the second member is in the first configuration and the end surface of the first member is aligned with a second marking of the plurality of spaced apart markings when the second member is in the second configuration, and wherein the handle of the first member and the handle of the second member when cooperatively engaged are lockable to maintain a selected exposure distance and angle of the tip.

17. A surgical instrument as recited in claim 16, wherein the handle of the first member includes a post having a threaded exterior surface, the handle of the second member including a post having a threaded interior surface that frictionally engages the threaded exterior surface of the post of the first member.

18. A surgical instrument as recited in claim 16, wherein the second member is formed of a shape memory material.

19. A surgical instrument as recited in claim 18, wherein the shape memory material is nitinol.

20. A surgical instrument, comprising:

a first member extending along a longitudinal axis between a first end having a first end surface and an opposite second end, the first member having an inner surface defining a passageway extending along the longitudinal axis and an outer surface, the passageway having a first opening at the first end of the first member and a second opening at the second end of the first member, the first member including a handle at the first end of the first member, the first member having a plurality of spaced apart indicators each correlating to a distance between a second end surface of the first member and a respective indicator of the plurality of spaced apart indicators; and a second member slidably disposed in the passageway of the first member and having a first end and an opposite second end with a tip, the second member including a handle at the first end, the handle of the first member and the handle of the second member being configured to cooperatively engage each other to limit movement of the second member within the passageway of the first member, the first end of the second member having a plurality of spaced apart markings indicating an exposure distance of the tip and a corresponding plurality of spaced apart indicia indicating an angle of the tip relative to the longitudinal axis of the first member, wherein at least a portion of the second end of the second member is formed of nitinol and is pre-bent, the second member having an inner surface defining a channel, the channel having a first opening at the first end of the second member and a second opening at the second end of the second member;

wherein the second member is movable between a first configuration in which the tip is disposed within the passageway and extends parallel to the longitudinal axis and a second configuration in which the tip extends through the second opening of the passageway and extends transverse to the longitudinal axis, wherein the first end surface of the first member is aligned with a first one marking of the plurality of spaced apart markings when the second member is in the first configuration and the first end surface of the first member is aligned with a second marking of the plurality of spaced apart markings when the second member is in the second configuration, wherein the tip extends at a first angle relative to the longitudinal axis when the second member is in the second configuration, wherein the second member is movable from the second configuration to a third configuration in which the tip extends through the second opening of the passageway and extends at a second angle relative to the longitudinal axis of the first member, the second angle being greater than the first angle, wherein the first end surface of the first member is aligned with a third marking of the plurality of spaced apart markings when the second member is in the third configuration, and wherein the handle of the first member and the handle of the second member when cooperatively engaged are lockable to maintain a selected exposure distance and angle of the tip.

* * * * *